US012558372B2

(12) United States Patent
Mollica et al.

(10) Patent No.: US 12,558,372 B2
(45) Date of Patent: Feb. 24, 2026

(54) POLYHYDROXYALKANOATES FOR USE IN THE PREVENTION OR TREATMENT OF AN OVERWEIGHT OR OBESITY CONDITION, OR OF METABOLIC DYSFUNCTIONS RELATED TO SAID CONDITION

(71) Applicant: BIO-ON S.P.A., San Giorgio di Piano (IT)

(72) Inventors: Maria Pina Mollica, Naples (IT); Paolo Saettone, San Giorgio di Piano (IT); Giovanna Trinchese, Naples (IT); Gina Cavaliere, Naples (IT); Giuseppina Mattace Raso, Naples (IT); Mauro Comes Franchini, San Giorgio di Piano (IT)

(73) Assignee: BIO ON S.P.A., Turin (IT)

( * ) Notice: Subject to any disclaimer, the term of this patent is extended or adjusted under 35 U.S.C. 154(b) by 1146 days.

(21) Appl. No.: 17/263,327

(22) PCT Filed: Jul. 24, 2019

(86) PCT No.: PCT/IB2019/056309
§ 371 (c)(1),
(2) Date: Jan. 26, 2021

(87) PCT Pub. No.: WO2020/021461
PCT Pub. Date: Jan. 30, 2020

(65) Prior Publication Data
US 2021/0161948 A1        Jun. 3, 2021

(30) Foreign Application Priority Data

Jul. 26, 2018    (IT) ......................... 102018000007524

(51) Int. Cl.
| | |
|---|---|
| *A61K 31/765* | (2006.01) |
| *A61K 9/00* | (2006.01) |
| *A61P 3/04* | (2006.01) |
| *C08G 63/06* | (2006.01) |

(52) U.S. Cl.
CPC .......... *A61K 31/765* (2013.01); *A61K 9/0053* (2013.01); *A61P 3/04* (2018.01); *C08G 63/06* (2013.01)

(58) Field of Classification Search
None
See application file for complete search history.

(56) References Cited

FOREIGN PATENT DOCUMENTS

| | | | |
|---|---|---|---|
| EP | 1098655 A2 | 5/2001 | |
| WO | 9841200 A1 | 9/1998 | |
| WO | WO-9932536 A1 * | 7/1999 | ............. A61K 47/34 |
| WO | 0004895 A2 | 2/2000 | |
| WO | WO-2014106026 A1 * | 7/2014 | ............. A23K 20/10 |

OTHER PUBLICATIONS

Sigma-Aldrich https://www.sigmaaldrich.com/specification-sheets/146/356/403105-BULK_____ALDRICH__.pdf(accessed Jun. 13, 2024). (Year: 2024).*
Peirson, L. et al. Treatment for overweight and obesity in adult populations: a systematic review and meta-analysis, CMAJ Open, 2014.DOI:10.9778/cmajo.20140012 (Year: 2014).*
Jones et al., The New Era of Drug Therapy for Obesity: The Evidence and the Expectations, Drugs (215) 75:935-945 2015 (Year: 2015).*
Rivera-Briso et al. Poly(3-Hydroxybutyrate-co-3-Hydroxyvalerate): Enhancement Strategies for Advanced Applications, Polymers 2018, 10, 732; doi: 10.3390/polym10070732. (Year: 2018).*
Fischer et al., "Effect of a Sodium and Calcium DL-β-Hydroxybutyrate Salt in Healthy Adults", Journal of Nutrition and Metabolism, vol. 2018, pp. 1-8.
A Hernandez-Aguilera et al., "Mitochondrial dysfunction: a basic mechanism in inflammation-related non-communicable diseases and therapeutic opportunities", Mediators Inflamm, 2013.
A. Lama et al., "Polyphenol-rich virgin olive oil reduces insulin resistance and liver inflammation and improves mitochondrial dysfunction in high-fat diet fed rats", Mol Nutr Food Res, Mar. 2017, vol. 61, No. 3, Epub Dec. 20, 2016.
C.K. Chakraborti, "Role of adiponectin and some other factors linking type 2 diabetes mellitus and obesity"; World J. Diabetes, 2015, vol. 6, pp. 1296-1308.
Dr. Simon F. Williams et al. "Applications of PHAs in Medicine and Pharmacy", Biopolyymers—Polyesters III: Applications and Commerical Products, Jan. 15, 2005, vol. 4, pp. 1-38, XP002789682.
G.L.S. Pawan et al. "Effect Of 3-Hydroxybutyrate in Obese Subjects On Very-Low-Energy Diets and During Therapeutic Starvation", Jan. 31, 1993, the whole document, [retrieved on Nov. 20, 2018] Retrieved from the Internet: URL:https://ac.els-cdn.com/S014067368391560X/1-s2.0-S014067368391560X-main.pdf?_tid=0277eb99-8cbd-4321-9976-88976234c422&acdnat=1542716720_b82be3233c0de763ec8f4fac52ff3222.

(Continued)

*Primary Examiner* — David J Blanchard
*Assistant Examiner* — Sarah J Chickos
(74) *Attorney, Agent, or Firm* — CANTOR COLBURN LLP

(57)        ABSTRACT

A polyhydroxyalkanoate (PHA) containing monomer units of 3-hydroxybutyrate for use, by oral administration, in the prevention or treatment of an overweight or obesity condition, or of metabolic dysfunctions related to the condition. A marked effect was observed on the reduction of the body weight, both in the case of a standard diet and in the case of a diet rich in fats, a reduction that can be attributed to an increase in lipid oxidation to the detriment of the deposit of excess lipids, as confirmed by the decrease in the body weight and by analyses of the body composition. A positive effect on the metabolic dysfunctions related to an overweight or obesity condition has also been verified, in particular on dyslipidemias, such as the blood level of low-density lipoproteins (LDL cholesterol) and triglycerides, as well as an improvement in the inflammatory state.

8 Claims, 7 Drawing Sheets

(56)                                References Cited

OTHER PUBLICATIONS

International Search Report issued Nov. 21, 2019 re: Application No. PCT/IB2019/056309, pp. 1-4, citing: EP 1 098 655 A2, Dr. Williams et al. "Applications of PHAs . . . ", Greaves MF et al. "Effect of . . . ".

M.P. Mollica et al., "Butyrate Regulates Liver Mitochondrial Function, Efficiency, and Dynamics in Insulin-Resistant Obese Mice", Diabetes, May 2017, vol. 66, No. 5, pp. 1405-1418.

T. Yamauchi et al., "Adiponectin stimulates glucose utilization and fatty-acid oxidation by activating AMP-activated protein kinase", Nat. Med., 2002, vol. 8, pp. 1288-1295.

World Health Organization (WHO), "Obesity and Overweight", Feb. 16, 2018, whole document, available on http://www.who.int/news-room/fact-sheets/detail/ obesity-and-overweight.

Written Opinion issued Nov. 21, 2019 re: Application No. PCT/IB2019/056309, pp. 1-6, citing: EP 1 098 655 A2, Dr. Williams et al. "Applications of PHAs . . . ", Greaves MF et al. "Effect of . . . ".

Y. Minokoshi et al., "Leptin stimulates fatty-acid oxidation by activating AMP-activated protein kinase", Nature, 2002, vol. 415, pp. 339-343.

* cited by examiner

POLYHYDROXYALKANOATES FOR USE IN THE PREVENTION OR TREATMENT OF AN OVERWEIGHT OR OBESITY CONDITION, OR OF METABOLIC DYSFUNCTIONS RELATED TO SAID CONDITION

TECHNICAL FIELD

The present disclosure relates to polyhydroxyalkanoates (PHA) for use in the prevention or treatment of an overweight or obesity condition, or of metabolic dysfunctions related to said condition.

BACKGROUND

Obesity is one of the main pathological conditions that afflict public health worldwide, as it is closely related to multiple pathologies that greatly reduce life expectancy. Epidemiological data estimate the onset of obesity in about 13% of the world population [Ref.1]. Excessive accumulation of body fat, due to an increase in caloric intake and/or an incorrect lifestyle, alters energy homeostasis, activating a complex network of signal pathways involved in inflammation or oxidative stress [Ref.2]. In both processes, a central role is played by mitochondrial dysfunction in the main high metabolic rate organs [Ref.3].

Obesity as a multifactorial pathology represents an important challenge to the research for the identification of therapeutic strategies that can replace or integrate with the current schemes provided in the clinic, sometimes accompanied by numerous undesired effects. The search for new compounds provided with a good tolerability profile can bring about great benefits to public health with a reduction in health spending. The identification of new molecules able to positively influence energy expenditure, with both central and peripheral mechanisms, and to modulate mitochondrial function, with consequent reduction in oxidative stress in high metabolic rate organs (liver, skeletal-muscle system and brain), could be promising candidates both in limiting the inflammatory process underlying obesity and in correcting the associated metabolic dysfunctions.

Various dietary supplements of natural origin are currently marketed that would be able to exercise a control of the body weight, in addition to certain beneficial effects on the metabolism, such as for example: dry extract of green coffee beans, piperine, chitosan associated with controlled amounts of chromium (mcg), dry extract of Garcinia Cambogia, and others. Their effectiveness in controlling the body weight is still controversial, besides having some side effects, such as those related to excessive caffeine intake (in the case of green coffee) or constipation (in the case of chitosan). Piperine intake is not recommended in subjects affected by gastritis, ulcer, gastroesophageal reflux or hypertension, while Garcinia Cambogia intake is discouraged for diabetics.

Polyhydroxyalkanoates (PHA), and in particular polyhydrobutyrate (PHB), are bacterial energy reserves. These polymers are not toxic in humans and can be used for the realisation of devices for surgery and other medical applications.

WO 00/04895 (Metabolix Inc.) refers to nutritional and therapeutic uses of 3-hydroxyalkanoate oligomers to increase the levels of ketone bodies in the blood of humans and other mammals, suitable for oral or parenteral administration. Such oligomers provide a source of ketone bodies in the form of linear or cyclic oligomers and/or derivatives of 3-hydroxy acids. Representative methods for preparing the derivatives of hydroxy acid oligomers include the direct degradatation of PHA in oligomer derivatives; polymerization of hydroxyalkanoates or related derivatives; and, gradual synthesis of hydroxyalkanoate oligomers which begins or ends with the modification of a terminal hydroxyalkanoate unit. Cyclic oligomers have advantageous properties, since they can lead to a sustained and/or controlled blood level of ketones for a period of hours. Blood levels with increasing ketones are useful for controlling seizures, controlling metabolic diseases, reducing protein catabolism, suppressing appetite, parenteral nutrition, increasing cardiac efficiency, treating diabetes and insulin-resistant states and treating effects of neurodegenerative disorders and epilepsy.

SUMMARY

The Applicant has studied the effects of the oral administration of PHA in mammals to verify the existence of possible beneficial effects on the control of the body weight and on other conditions related to an accumulation of body fat that can manifest itself as overweight or as real obesity. Within the context of these studies, the Applicant has surprisingly found that the oral administration of a PHA containing monomer units of 3-hydroxybutyrate, in particular of a P3HB, has a marked effect on the reduction of the body weight, both in the case of a standard diet and in the case of a diet rich in fats, a reduction that can be attributed to an increase in lipid oxidation to the detriment of the deposit of excess lipids, as confirmed by the decrease in the body weight and by analyses of the body composition. The Applicant has also found that the oral administration of a PHA containing 3-hydroxybutyrate monomer units has a positive effect on the metabolic dysfunctions related to an overweight or obesity condition, in particular on dyslipidemias, such as the blood level of low-density lipoproteins (LDL cholesterol) and triglycerides, as well as an improvement in the inflammatory state, as demonstrated by the reduced levels of TNF-α (Tumor Necrosis Factor) and leptin, which is accompanied by an increase in the concentration of adiponectin, which leads to an increase in the oxidation of fatty acids.

Therefore, according to a first aspect, the present disclosure refers to a polyhydroxyalkanoate (PHA) containing 3-hydroxybutyrate monomer units for use, by oral administration, in the prevention or treatment of an overweight or obesity condition, or of metabolic dysfunctions related to said condition.

(upper left) the oxidation rate of fatty acids, using succinate as an energy substrate both in the absence (state 4) and in the presence (state 3) of ADP, (upper right) the oxidation rate of fatty acids, using palmitoyl-carnitine as a substrate both in the absence (state 4) and in the presence (state 3) of ADP, (bottom center) the measurement of the activity of the carnitine-palmitoyl transferase (CPT) enzyme.

Figure 6:
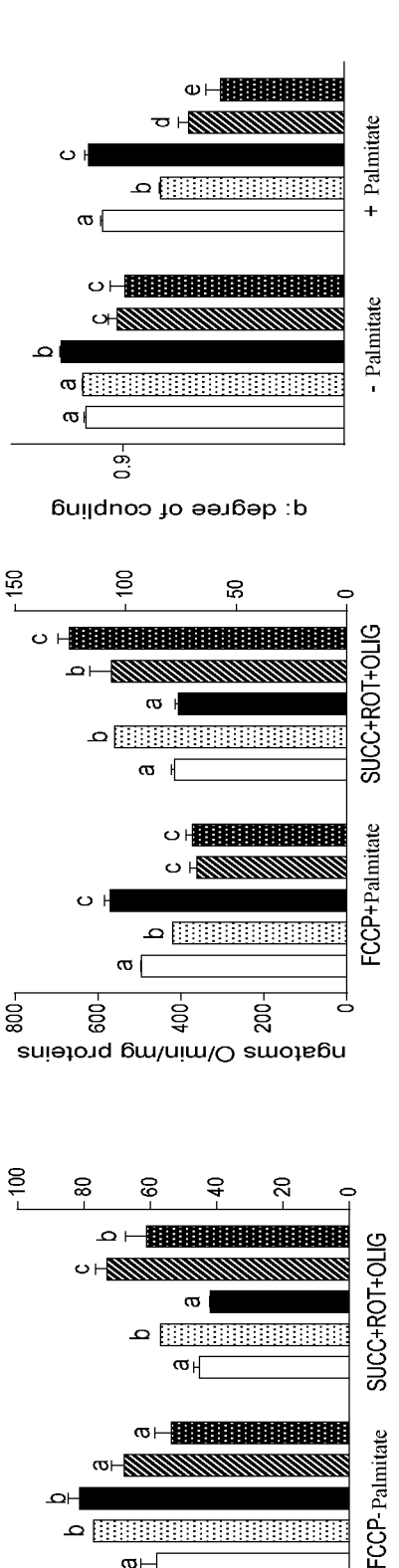

FIG. 6 includes three graphs showing for groups 1-5 the oxygen consumption rate in the presence of succinate and an uncoupling agent (FCCP, left and center) and the degree of mitochondrial coupling (right).

Figure 7:
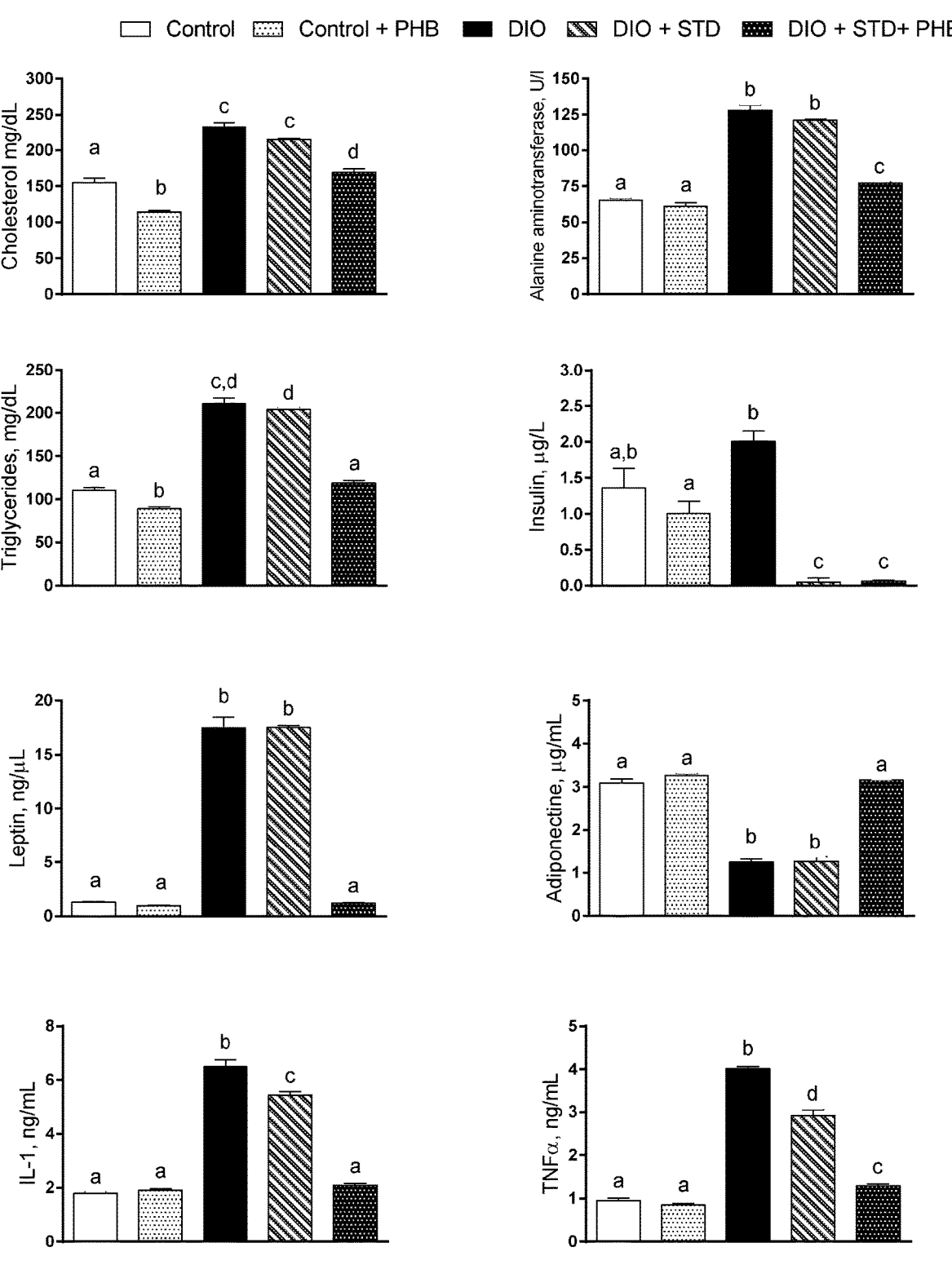

FIG. 7 includes eight graphs reporting the following parameters at blood level after the treatment of groups 1-5: IL-1 (bottom left), leptin (second from bottom left), triglycerides (second from top, left), cholesterol (top left), TNF-$\alpha$ (bottom right), adiponectine (second from bottom right), insulin (second from top right), alanine aminotransferase (top right).

DETAILED DESCRIPTION OF THE DISCLOSURE

Preferably, PHA is a poly-3-hydroxybutyrate homopolymer (P3HB) or a copolymer containing at least 20% by mole of 3-hydroxybutyrate monomer units, the remaining being hydroxyalkanoate monomer units different from 3-hydroxybutyrate.

Oral administration can for example be carried out in the form of an aqueous suspension of PHA to a subject affected by obesity. Alternatively, the oral administration can be a food administration, that is as a food supplement, which can be directed to most of the population wishing to achieve an effect on weight control.

The PHA is generally a PHA as such, that is obtained from the fermentation of an organic substrate through a PHA-producing microorganism, without any chemical modification to the PHA structure, such as that described in WO 00/04895 mentioned above to obtain low molecular weight oligomers. The PHA can only be subjected to a purification phase, which has the purpose of eliminating secondary products that may be present in PHAs and be unsuitable for oral administration, such as surfactants and cellular residues. After purification, the PHA usually has a purity level of at least 99.5%.

PHAs suitable for the present disclosure are produced by microorganisms isolated from natural environments or even from genetically modified microorganisms, which act as carbon and energy reserves and which are accumulated by various species of bacteria in unfavourable growth conditions and in the presence of an excess carbon source. PHAs can be synthesized and accumulated from about 300 different microbial species, included among more than 90 types of Gram-positive and Gram-negative bacteria, such as for example *Bacillus, Rhodococcus, Rhodospirillum, Pseudomonas, Alcaligenes, Azotobacter, Rhizobium*. In cells, PHAs are stored in the form of microgranules, whose size and number per cell varies in the different species of bacteria.

In general, PHAs that are suitable for the present disclosure are homopolymers consisting of 3-hydroxybutyrate monomer units:

$$\text{—O—CH(CH}_3)\text{—CH}_2\text{—CO—} \qquad (I)$$

or copolymers of 3-hydroxybutyrate monomer units with at least one hydroxyalkanoate monomer unit having the formula $$\text{—O—CHR}_1\text{—(CH}_2)_n\text{—CO—} \qquad (II)$$

wherein:

R$_1$ is selected from: —H and C$_1$-C$_{12}$ alkyls;

n is zero or an integer comprised in the range from 1 to 6, and is preferably 1 or 2; provided that, when R$_1$ is methyl, n is different from 1. Preferably, R$_1$ is methyl or ethyl. Preferably, n is 1 or 2.

In the case of a copolymer, it contains preferably at least 20% by mole, more preferably at least 30% by mole, of 3-hydroxybutyrate monomer units, the remaining being hydroxyalkanoate monomer units different from 3-hydroxybutyrate. In such copolymers, the amount of 3-hydroxybutyrate monomer units is generally equal to or lower than 99% by mole, preferably equal to or lower than 90% by mole.

Particularly preferred repetitive units having the formula (II) are those deriving from: 4-hydroxybutyrate, 3-hydroxyvalerate, 3-hydroxyhexanoate, 3-hydroxyoctanoate, 3-hydroxyundec-10-enoate, 4-hydroxyvalerate.

In the case of PHA copolymers, they are preferably selected from: poly(3-hydroxybutyrate-co-3-hydroxyvalerate) (P3HBV), poly(3-hydroxybutyrate-co-3-hydroxyhexanoate) (P3HBH), poly(3-hydroxybutyrate-co-4-hydroxybutyrate, poly(3-hydroxybutyrate-co-3-hydroxyvalerate-co-4-hydroxyvalerate (PHBVV), or mixtures thereof.

PHAs suitable for the present disclosure preferably have an average molecular weight (M$_w$) comprised in the range from 5,000 to 1,500,000 Da, more preferably from 100,000 to 1,000,000 Da. The average molecular weight can be determined according to known techniques, in particular by means of GPC analysis (Gel Permeation Chromatography).

With regard to the production of PHAs, it is preferably obtained from microbial fermentation of an organic substrate (for example carbohydrates or other fermentable substrates, such as glycerol) using a strain of microorganisms capable of producing PHAs, and the subsequent recovery of the PHAs from the cell mass. For further details, reference can be made, for example, to patent applications WO 99/23146, WO 2011/045625 and WO 2015/015395. Suitable substrates for the production of PHAs by fermentation can be obtained in particular from the processing of plants, for example juices, molasses, pulps from the processing of sugar beet, sugar cane. These substrates generally contain, in addition to sucrose and other carbohydrates, organic growth factors, nitrogen, phosphorus and/or other minerals which are useful as nutrients for cell growth. An alternative is glycerol, a low-cost organic carbon source, as it is a by-product of biodiesel production (see, for example, U.S. Pat. No. 8,956,835 B2).

Since PHAs suitable for the present disclosure are not water-soluble, they can be administered in the form of aqueous suspensions, wherein PHA is in the form of suspended particles, preferably having an average size comprised in the range from 0.1 $\mu$m to 1,000 $\mu$m, more preferably from 1 $\mu$m to 500 $\mu$m. These sizes can be determined according to techniques that are well known in the art, such as systems for detecting the size of suspended particles with laser detectors, known as dynamic light scattering techniques (DLS) (see ISO 13320-2009 standard). As an alternative, electron microscope images (SEM) can be used, which are digitally analysed according to well known techniques.

Alternatively, the PHA can be administered as a functional component in different pharmaceutical products, in which PHA particles can be suspended. Some examples are gel sachets, capsules, powder sachets and pills.

When administered as a food supplement, the PHA can be added to other edible products, such as functional drinks, fruit jellies, powders for resuspension in any liquid food matrix, cereal bars, powdered formulas for breakfast, biscuits, jelly sweets (jelly beans), chewing gum, chocolate, fermented milk, ice cream, chips, bread or noodle.

As regards the PHA dosage to obtain a significant effect in the prevention or treatment of an overweight or obesity condition, or of metabolic dysfunctions related to this condition, obviously it depends on the condition of the subject, on the diet to which the subject is subjected, on the predisposing genetic conditions, and on the presence of external factors that can influence the control of the body weight (physical activity, environmental conditions, etc.). Usually, the daily dosage can generally be equal to or higher than 0.3 g/kg of body weight, preferably equal to or higher than 0.4 g/kg of body weight. With regard to an upper limit in the dosage, it is recommended to have a daily dosage equal to or lower than 2.5 g/kg of body weight, preferably equal to or lower than 1.5 g/kg of body weight.

The following examples are provided merely to illustrate the present disclosure and should not be construed to limit the scope of protection defined by the claims.

Examples

C57BL/6 male mice (6 weeks of age) were placed in standard plexiglas cages at constant temperature (21±1° C.) with relative humidity of 60±5% and with light-dark cycles of 12 hours. Water and food pellets (standard diet and fat diet) were supplied to animals ad libitum. The animals were divided into the following groups:

(1) animals fed on a standard diet (STD);

(2) animals fed on a fat diet (Teklad #93075) (DIO).

The characteristics of the two diets were as follows:

(1) Standard Diet (STD):

Energy density: 15.88 kJ/g diet;

Proteins: 29% (J/J);

Lipids: 10.6% (J/J);

Carbohydrates: 60.4% (J/J)

(2) Fat diet (DIO):

Energy density: 22 kJ/g diet

Proteins: 21.2% (J/J);

Lipids: 54.8% (J/J);

Carbohydrates: 24% (J/J)

The dietary treatment with DIO lasted 12 weeks, the time necessary for establishment of the obese phenotype [Ref. 2]. At the end of 12 weeks, the animals fed on the DIO diet were brought back to a standard diet and a group of them was treated with PHB (5 mg/g body weight) by means of a gavage for 5 days. More precisely, the PHB was P3HB. Animals not treated with PHB received only the medium ($H_2O$) via gavage.

The animals were then subdivided into the following groups:

Group 1: animals fed on a standard diet (Control, n=6);

Group 2: animals fed on a standard diet+PHB (5 mg/g body weight), (Control+PHB, n=6)

Group 3: animals fed on a fat diet (DIO, n=6)

Group 4: animals fed on a fat diet, brought back on a standard diet (DIO-STD, n=6)

Group 5: animals fed on a fat diet, brought back on a standard diet+PHB (5 mg/g body weight), (DIO-STD+ PHB, n=6).

Figure 1:
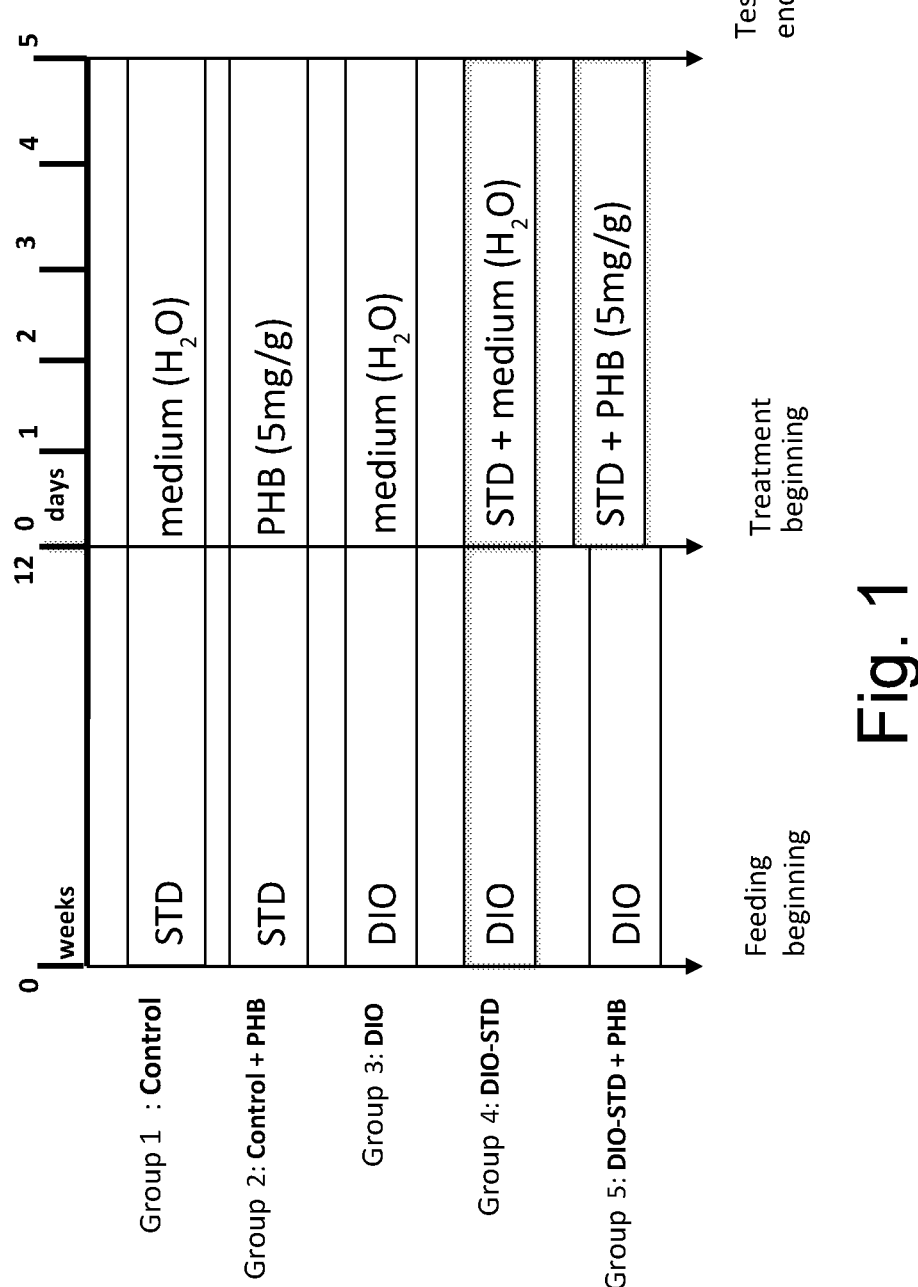
FIG. 1 shows the temporal scheme of the diets for groups 1-5: control, control+PHB, DIO, IDO-STD, DIO-STD+PHB.

FIG. 1 appended to the present description shows the temporal scheme of the diets for the different groups.

Figure 2:
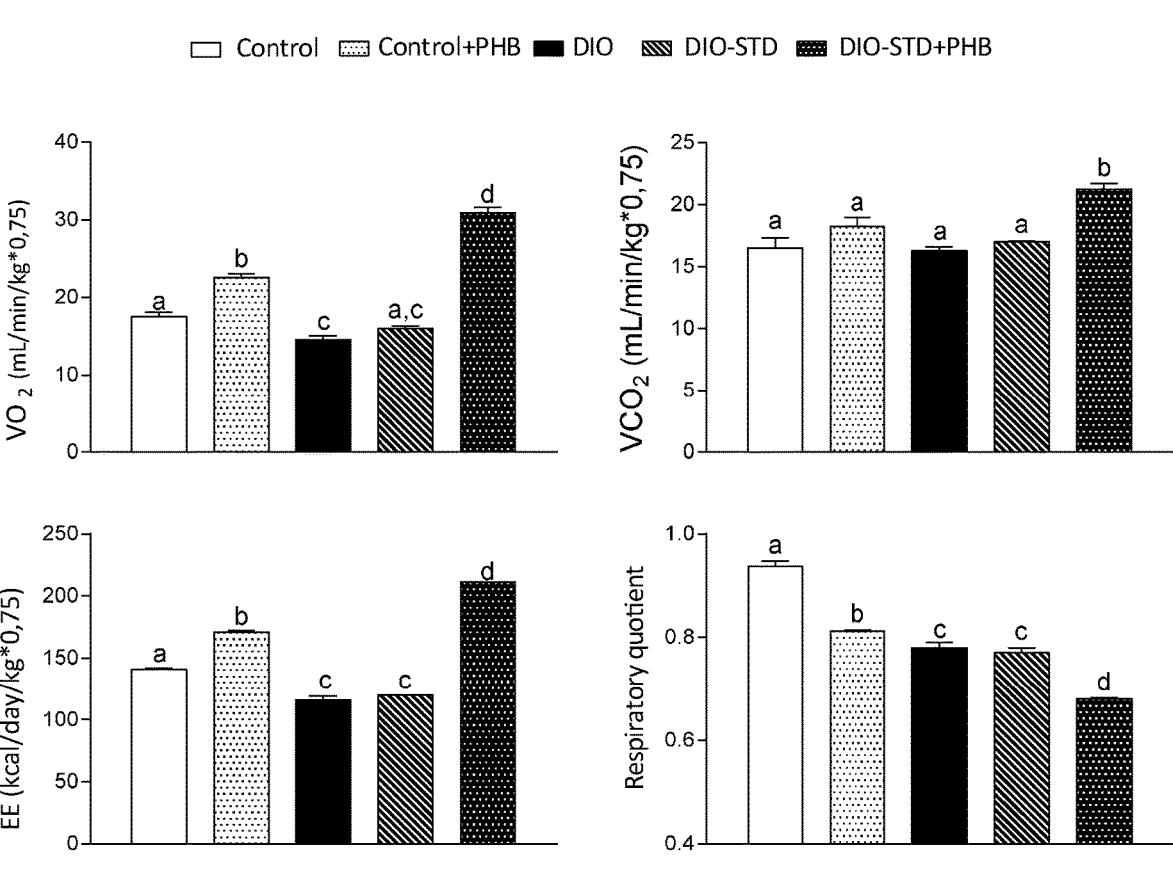
FIG. 2 includes four graphs showing the post-treatment results for groups 1-5 with respect to: $VO_2$ (oxygen consumption, upper left), $VCO_2$ (carbon dioxide production, upper right), EE (energy expenditure, bottom left), and respiratory quotient (bottom right).

At the end of the experimental period, the measurement of the resting metabolic rate (RMR) was carried out, by using an open circuit metabolimeter, in a chamber at 24° C. The animals were allowed to adapt in the measuring cage for about an hour, subsequently their body metabolism was determined in terms of oxygen consumption (VO2) and production of carbon dioxide ($CO_2$) and, indirectly, the quality of the oxidation of the different energy substrates was assessed by determination of the respiratory quotient. The results derived from the measurement of basal metabolism highlights a significant increase in $O_2$ consumption, $CO_2$ production and energy expenditure in animals fed on the DIO diet and treated with PHB. Further, a significant decrease in the respiratory quotient was found in groups treated with PHB if compared to groups that did not receive any administration, indicating a greater lipid oxidation in these animals. The results are reported in FIG. 2.

Further, during the entire period of the treatment, the body weight and the food intake were monitored in order to calculate the weight gain and the energy introduced in the form of food. At the end of the treatment, the body composition of the carcass was analysed in terms of lipid content and water content and an analysis of the energy balance was performed.

Figure 3:
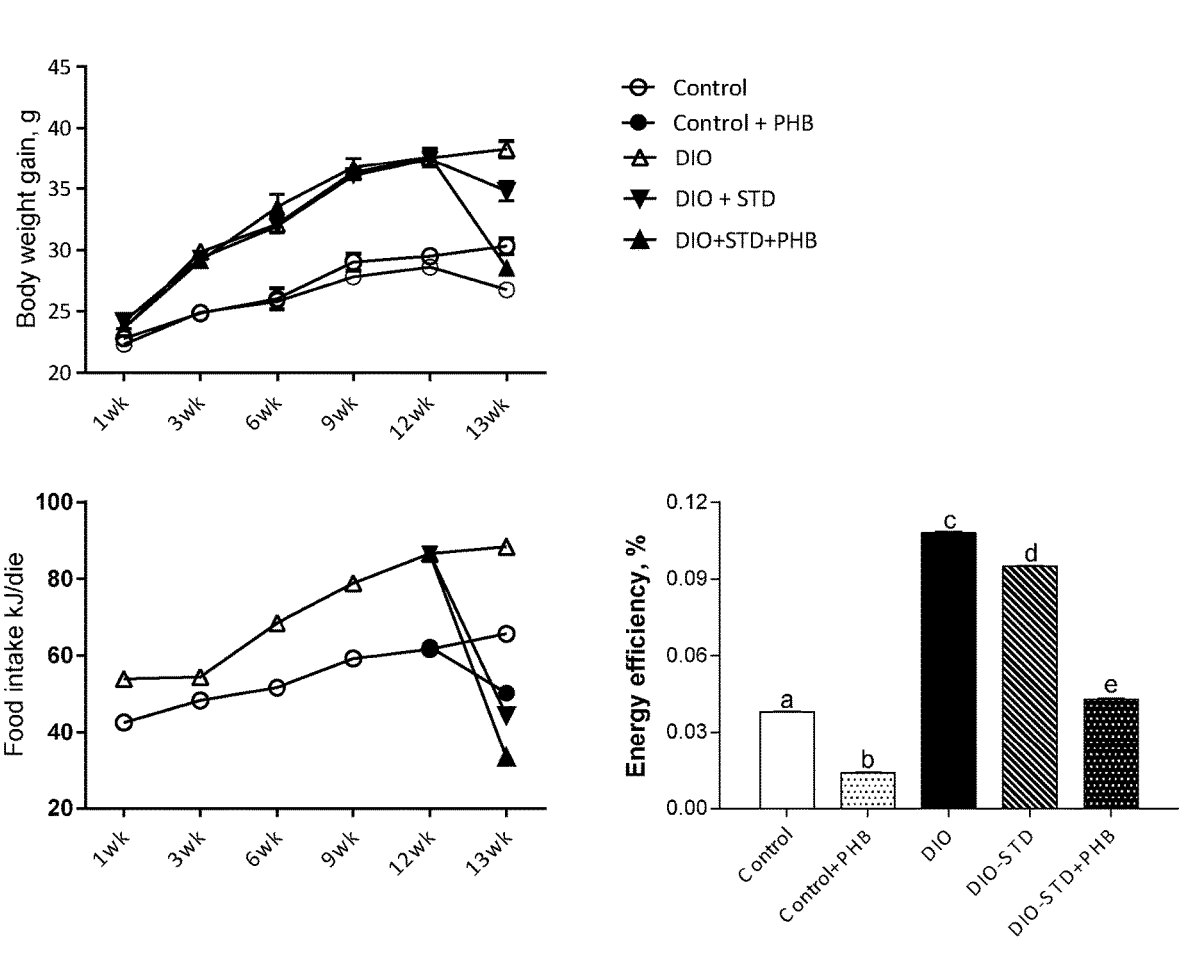
FIG. 3 includes three graphs showing the change of body weight (top), food intake (bottom left), and energy efficiency (bottom right) during the entire period of treatment for groups 1-5.

The results obtained show that, at the end of the first 12 weeks, the animals fed on the DIO diet, consequently to a higher caloric intake, show a body weight that is higher than the group fed on a standard diet. See the results reported in FIG. 3.

Treatment with PHB led to a decrease in caloric intake in both groups of animals. Consequently, a significant reduction in body weight was found in animals that received PHB administration. Metabolic efficiency, calculated as the ratio between body weight gain and energy intake, increases following an intake of the DIO diet and a decrease following the treatment with PHB. These results, according to the increase in energy expenditure, indicate that in animals treated with PHB most of the energy intake is mainly directed towards oxidation rather than deposit, as confirmed by the decrease in the body weight and by analyses of the body composition.

The results of the thirteenth week are summarized as follows.

(a) Group 1—animals fed on a standard diet (Control, n=6): weight increase +2.7%;

(b) Group 2: animals fed on a standard diet+PHB (5 mg/g body weight), (Control+PHB, n=6): weight reduction −6.5%

(c) Group 3—animals fed on a fat diet (DIO, n=6): weight increase +1.8%

(d) Group 4: animals fed on a fat diet, brought back on a standard diet (DIO-STD, n=6): weight reduction −7%

(e) Group 5: animals fed on a fat diet, brought back on a standard diet+PHB (5 mg/g body weight), (DIO-STD+ PHB, n=6): weight reduction −25%

Figure 4:
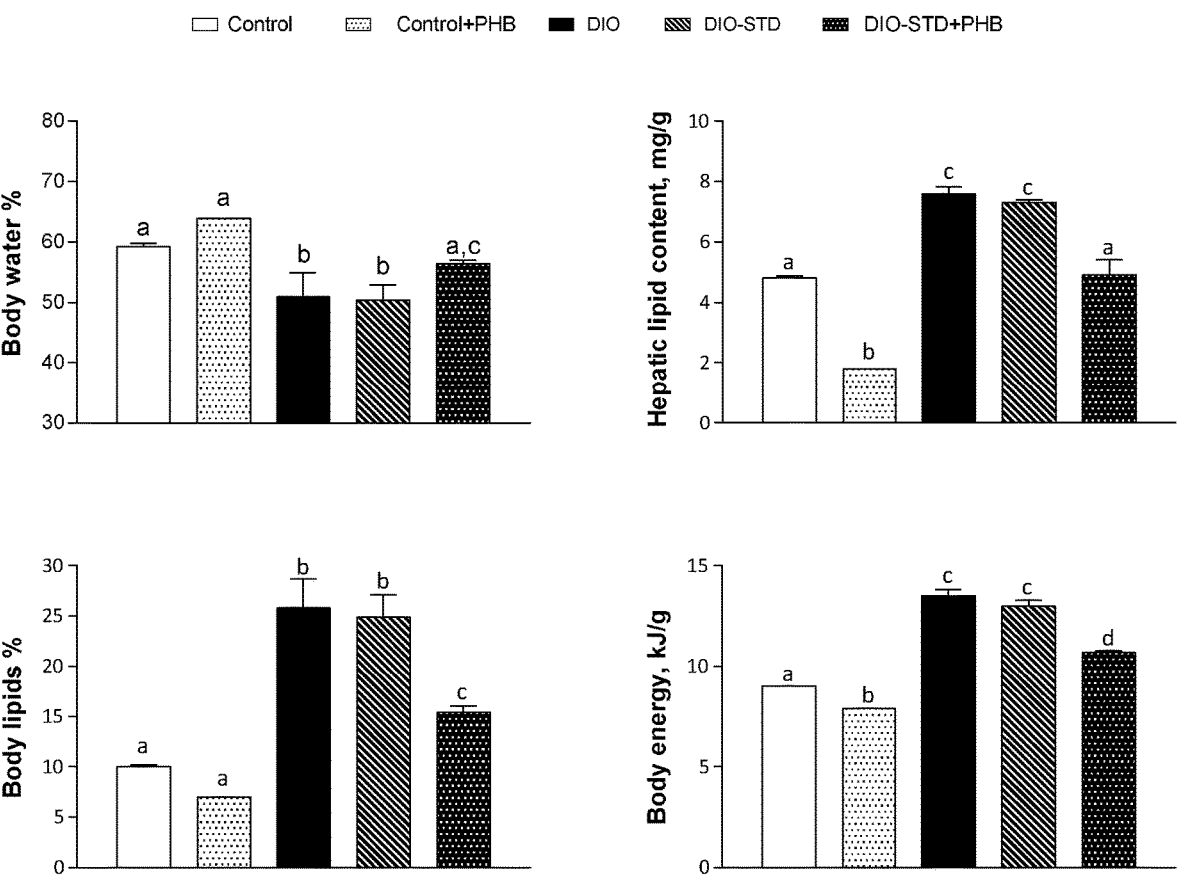
FIG. 4 includes four graphs showing the analysis of the body composition after the treatment of groups 1-5 with respect to: body water % (upper left), hepatic lipid content (upper right), body lipids % (lower left), body energy (lower right).

The analysis of the body composition showed an increased lipid percentage in rats fed on DIO diet with respect to those fed on a standard diet. The results are reported in FIG. 4. The supplement with PHB resulted in a slight reduction in the lipid content, both at body and liver level, in the standard group while a significant decrease was observed in animals of the DIO group. According to the variations in the lipid content, a reduced percentage of body water was found in animals fed on DIO diet, restored following the treatment with PHB, associated with a decrease in the energy content of the carcass.

Since the variations in body energy efficiency are linked to the variations in the mitochondrial efficiency of the single organs in the use of energy substrates and the liver is one of the central high metabolic rate organs of body metabolism, it was considered interesting to analyse the effect of PHB administration on hepatic mitochondrial energy efficiency and on the oxidation rate of fatty acids, isolating the mitochondria by means of appropriate experimental protocols.

Figure 5:
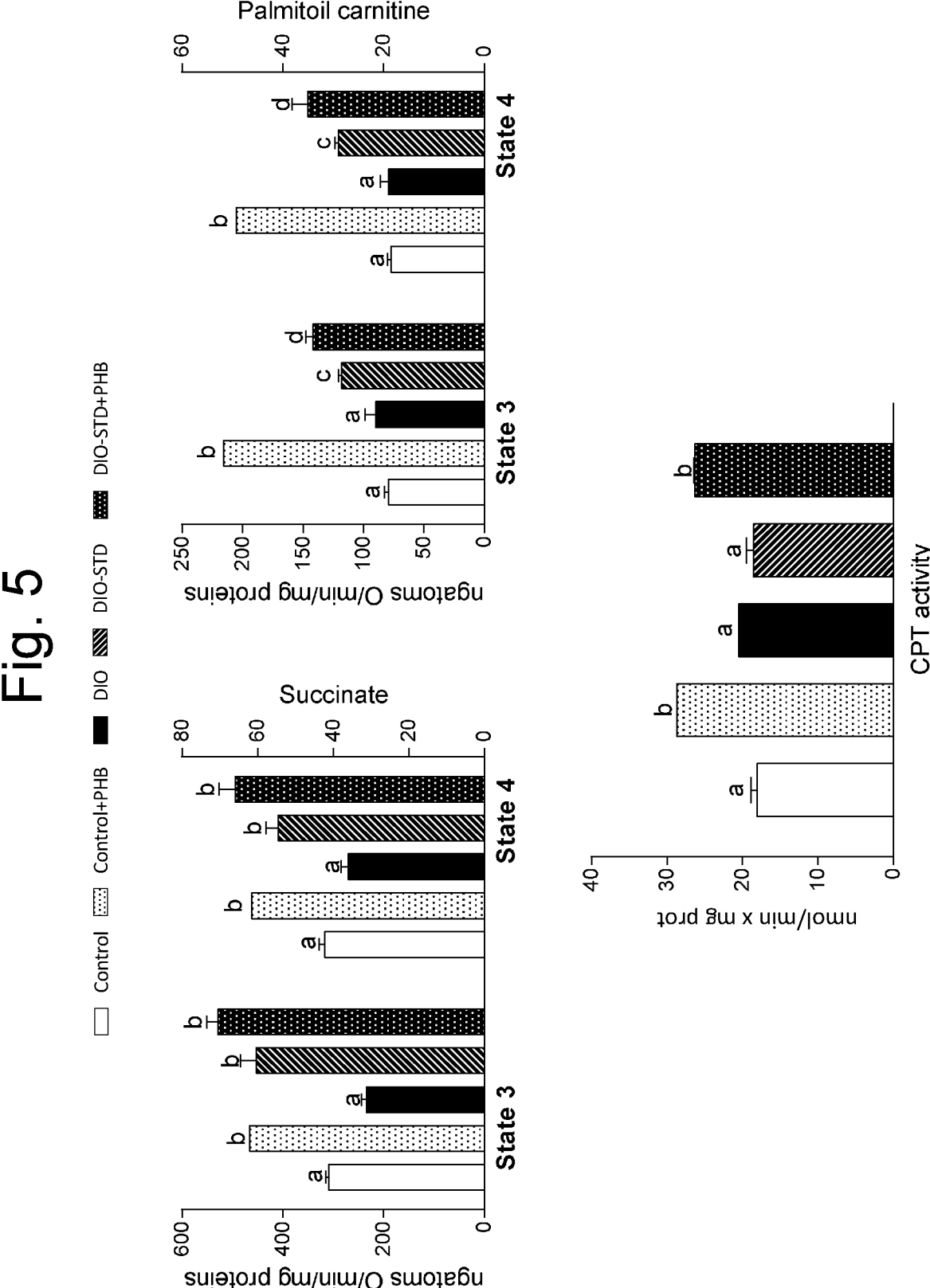
FIG. 5 includes three graphs showing for groups 1-5.

A significant improvement in hepatic mitochondrial function, using succinate as an energy substrate both in the absence (state 4) and in the presence (state 3) of ADP, was found in animals that received PHB administration, both in the standard group and in the DIO group. The results are reported in FIG. 5. The oxidation rate of fatty acids, calculated using palmitoyl-carnitine as a substrate, is increased in both state 4 and state 3 in treated rats with respect to groups that did not receive any PHB. This result is further strengthened by the measurement of the activity of the carnitine-palmitoyl transferase (CPT) enzyme responsible for the transfer of fatty acids into the mitochondrial compartment, whose activity was significantly higher in the groups that received PHB administration, if compared to the other experimental groups. An increase in the oxidation rate and CPT activity leads to a reduction in lipid deposits, as demonstrated by the measurement of hepatic and body lipid content. These results demonstrate for the first time that PHB administration improves the ability to use fats as an energy substrate and confirms that a large part of the energy introduced could be dissipated through an increased metabolic activity.

Another mechanism by which the supplement with PHB contributes to reducing fat accumulation can be explained through a decrease in mitochondrial metabolic efficiency. The latter can be defined as a measure of the entity with which the organism obtains energy in the form of compounds with high energy content (ATP) starting from the nutrients introduced with food. The metabolic efficiency comprises, therefore, the coupling between the oxidation of the substrates and the ATP synthesis. Starting from the assessment of oxygen consumption rate, in the presence of succinate and an uncoupling agent (FCCP) it was possible to determine the degree of mitochondrial coupling (q) [Ref. 4].

This parameter is significantly reduced in the groups treated with PHB, indicating that, given the same ATP produced, it is necessary to oxidise a greater amount of substrates which will consequently be removed from the deposit (see the results reported in FIG. 6).

Therefore, a lower mitochondrial metabolic efficiency results in a thermogenic effect which leads to a greater energy expenditure in the form of heat, justifying the reduction of body weight gain and lipid deposits.

Following the treatment with PHB, in addition to the beneficial effects found on the reduction of body weight and lipid content probably due, at least in part, to the modulation of energy expenditure and hepatic mitochondrial metabolic efficiency, improvements of some parameters were found at blood level. In particular, an improvement in dyslipidemia (cholesterol, triglycerides) and an improvement in the inflammatory state (TNF-$\alpha$, IL-1, leptin, adiponectin, ALT) were found. Finally, it has been demonstrated that the modulation of lipid metabolism can be related to the balance between the leptin and adiponectin levels (see the results reported in FIG. 7). These two hormones, both released by adipose tissue, are not only involved in lipid metabolism and in controlling energy homeostasis, but also in modulating the inflammatory state [Ref. 5 and 6]. As the fat mass increases, there is an increase in leptin levels and a reduction in adiponectin levels. In this study, according to the reduction of lipid deposits, a decrease in leptin levels and an increase in adiponectin concentration was found in the group fed on the DIO diet and treated with PHB. In some animal models, the increase in adiponectin concentration is associated with an increase of fatty acid oxidation. Further, adiponectin secretion is inhibited by several factors including high levels of TNF-$\alpha$ and oxidative stress [Ref. 7]. Our data, showing an increase in adiponectin concentration in the DIO group treated with PHB, associated with lower levels of TNF-$\alpha$, may be indicative of a lower degree of an inflammatory status in these animals, indicating that the treatment with PHB could be useful in improving the metabolic dysfunctions associated with inflammation.

The invention claimed is:

1. A method for reducing fat accumulation in a mammal, the method comprising oral administration to the mammal of poly-3-hydroxybutyrate (P3HB), wherein the P3HB has a weight average molecular weight ($M_w$) in the range from 100,000 to 1,500,000 Da, as determined by Gel Permeation Chromatography.

2. The method according to claim 1, wherein the P3HB has a weight average molecular weight ($M_w$) in the range from 100,000 to 1,000,000 Da.

3. The method according to claim 1, wherein the oral administration is an administration of an aqueous suspension of the PH3B to a mammal affected by obesity.

4. The method according to claim 1, wherein the oral administration is a food administration.

5. The method according to claim 1, wherein the oral administration has a daily dosage equal to or higher than 0.3 g/kg body weight.

6. The method according to claim 1, wherein the oral administration has a daily dosage equal to or lower than 2.5 g/kg body weight.

7. The method according to claim 5, wherein the oral administration has a daily dosage equal to or higher than 0.4 g/kg body weight.

8. The method according to claim 6, wherein the oral administration has a daily dosage equal to or lower than 1.5 g/kg body weight.

\* \* \* \* \*